United States Patent [19]

Wehinger et al.

[11] Patent Number: 4,551,467

[45] Date of Patent: Nov. 5, 1985

[54] VASODILATING CYANOALKYL ESTERS OF 1,4-DIHYDROPYRIDINES

[75] Inventors: Egbert Wehinger, Velbert; Friedrich Bossert, Wuppertal; Wulf Vater, Leverkusen; Kurt Stoepel, Wuppertal, all of Fed. Rep. of Germany

[73] Assignee: Bayer Aktiengesellschaft, Leverkusen, Fed. Rep. of Germany

[21] Appl. No.: 83,884

[22] Filed: Oct. 11, 1979

[30] Foreign Application Priority Data

Oct. 31, 1978 [DE] Fed. Rep. of Germany ....... 2847236

[51] Int. Cl.$^4$ ................. C07D 211/90; C07D 401/04; A61K 31/455
[52] U.S. Cl. .................................... 514/334; 514/356; 546/321; 546/258; 546/257
[58] Field of Search ............... 546/298, 267, 321, 258, 546/257; 424/263, 266; 514/356

[56] References Cited

U.S. PATENT DOCUMENTS

| | | | |
|---|---|---|---|
| 3,883,540 | 5/1975 | Meyer et al. | 546/321 |
| 3,923,818 | 12/1975 | Bossert et al. | 546/321 |
| 4,044,141 | 8/1977 | Bossert et al. | 546/298 |
| 4,284,634 | 8/1981 | Sato | 546/286 |
| 4,307,103 | 12/1981 | Sato et al. | 546/321 |

*Primary Examiner*—Henry R. Jiles
*Assistant Examiner*—Dale A. Bjorkman
*Attorney, Agent, or Firm*—Sprung, Horn, Kramer & Woods

[57] ABSTRACT

The invention relates to 1,4-dihydropyridines as well as methods for the preparation of said 1,4-dihydropyridines and compositions contained therein. The invention also includes the use of said compounds and compositions for influencing circulation.

16 Claims, No Drawings

VASODILATING CYANOALKYL ESTERS OF 1,4-DIHYDROPYRIDINES

The present invention relates to certain new 1,4-dihydropyridine compounds, to processes for their production and to their use as agents which influence the circulation.

It has already been disclosed that diethyl 1,4-dihydro-2,6-dimethyl-4-phenyl-pyridine-3,5-dicarboxylate is obtained when ethyl benzylideneacetoacetate is reacted with ethyl β-amino-crotonate or ethyl acetoacetate and ammonia (Knoevenagel, Ber. dtsch. Chem. Ges. 31, 743 (1898)).

It is also known that certain 1,4-dihydropyridines possess interesting pharmacological properties (F. Bossert and W. Vater, Naturwissenschaften 58, 578 (1971)).

According to the present invention there are provided compounds which are 1,4-dihydropyridines of the general formula

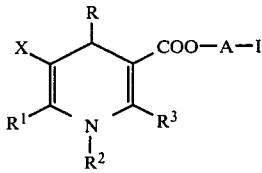

or a salt thereof in which

R denotes an aryl radical or denotes a heterocyclic radical selected from thienyl, furyl, pyrryl, pyrazolyl, imidazolyl, oxazolyl, isoxazolyl, thiazolyl, pyridyl, pyridazinyl, pyrimidyl, pyrazinyl, quinolyl, isoquinolyl, indolyl, benzimidazolyl, quinazolyl and quinoxalyl, the aryl radical or the heterocyclic radical optionally containing 1, 2 or 3 identical or different substituents selected from phenyl, alkyl, alkenyl, alkinyl, alkoxy, alkenyloxy, alkinyloxy, alkylene, dioxyalkylene, halogen, trifluoromethyl, trifluoromethoxy, hydroxyl, amino, alkylamino, nitro, cyano, azido, carboxyl, carbalkoxy, carboxamido, sulphonamido and $SO_m$-alkyl (m is 0, 1 or 2), $R^1$ and $R^3$ are identical or different and denote a hydrogen atom, a straight-chain or branched alkyl radical, an aryl radical or an aralkyl radical, $R^2$ denotes a hydrogen atom or a straight-chain or branched alkyl radical, which is optionally interrupted in the alkyl chain by one or two oxygen atoms, or denotes an aryl or aralkyl radical, A denotes a straight-chain, branched or cyclic alkylene group with up to 12 carbon atoms, which is optionally substituted by an α-, β- or γ-pyridyl group or by an aryl group, which, in turn, is optionally substituted by halogen, cyano, dialkylamino, alkyl, alkoxy, trifluoromethyl or nitro, Y denotes an azido, nitro or nitrile group or denotes an ester group of the formula —$COOR^4$, in which $R^4$ denotes an alkyl radical with up to 8 carbon atoms or denotes an aralkyl radical, or Y denotes a group of the formula

in which $R^5$ denotes a straight-chain or branched or cyclic saturated or unsaturated aliphatic hydrocarbon radical with up to 12 carbon atoms or denotes an aryl radical, which, in turn, is optionally substituted by halogen, alkyl, alkoxy, trifluoro- methyl, nitro, cyano or dialkylamino, and X(a) denotes a group of the formula —$COR^6$, in which $R^6$ denotes optionally substituted alkyl, aryl or aralkyl or an amino, monoalkylamino or dialkylamino group, or (b) denotes a group of the formula —$COOR^7$, in which $R^7$ denotes a straight-chain, branched or cyclic, saturated or unsaturated hydrocarbon radical, which is optionally interrupted in the chain by an oxygen atom or a sulphur atom or the —SO— or —$SO_2$ group and/or which is optionally substituted by one or two trifluoromethyl groups or by a phenyl, phenoxy, phenylthio or phenylsulphonyl group, which, in turn, is optionally substituted by halogen, cyano, dialkylamino, alkoxy, alkyl, trifluoromethyl or nitro, or which is optionally substituted by an α-, β- or γ-pyridyl group or is optionally substituted by an amino group, this amino group carrying two identical or different substituents selected from alkyl, alkoxyalkyl, aryl and aralkyl and these substituents optionally forming, together with the nitrogen atom, a 5-membered to 7-membered ring, which optionally contains, as a further hetero-atom, an oxygen or sulphur atom or the N-alkyl grouping, or (c) denotes a group of the formula —COO—A'—Y', it being possible for this group to be identical or different to —COO—A—Y and in which A' and Y' have any of these meanings given for A and Y, respectively, or (d) denotes a group of the formula —$S(O)_r$—$R^8$, in which r is 0, 1 or 2 and $R^8$ denotes a straight-chain, branched or cyclic, saturated or unsaturated aliphatic hydrocarbon radical which is optionally interrupted in the chain by 1 oxygen atom and/or is optionally substituted by a phenyl, phenoxy, phenylthio or phenylsulphonyl group, which, in turn, is optionally substituted by halogen, cyano, dialkylamino, alkoxy, alkyl, trifluoromethyl or nitro, or which is optionally substituted by an α-, β-or γ-pyridyl group or by an amino group, this amino group carrying two identical or different substituents selected from alkyl, alkoxyalkyl, aryl and aralkyl and these substituents optionally forming, together with the nitrogen atom, a 5-membered to 7-membered ring, which optionally contains, as a further hetero-atom, an oxygen or sulphur atom or the N-alkyl grouping, or in which $R^8$ denotes an aryl radical which optionally contains 1 to 3 identical or different substituents selected from alkyl, alkoxy, halogen, cyano, trifluoromethyl, trifluoromethoxy, dialkylamino and nitro.

As used herein and unless otherwise specified the term aryl preferably denotes a mono-or bi-cyclic carbocyclic grouping, such as phenyl, bi-phenyl or naphthyl; the terms alkyl, alkenyl, alkinyl, alkoxy, alkenyloxy dialkyemaine, alkylamine, carboalkoxy or $SO_m$-alkyl preferably denote a grouping wherein the hydrocarbon moiety contains up to 12 carbon atoms; the terms alkylene and dioxyalkylene preferably denote groupings having up to 12, especially up to 6 carbon atoms; the term halogen is preferably chlorine, fluorine or bromine; the term aralkyl preferably denotes a grouping wherein the aryl portion is as defined immediately above and the alkyl portion contains up to 5 carbon atoms.

According to the present invention there is further provided a process for the production of a compound according to the present invention in which (A) a ylidene compound of the general formula $$R-CH=C\begin{matrix}X\\COR^1\end{matrix} \qquad (II)$$

in which

R, R$^1$ and X have the above-mentioned meanings is reacted with an enaminocarboxylic acid ester of the general formula $$\begin{matrix}R^3-C=CH-COO-A-Y\\|\\R^2NH\end{matrix} \qquad (III)$$

in which

R$^2$, R$^3$, A and Y have the above-mentioned meanings, optionally in the presence of an inert organic solvent, or (B) a ylidene compound of the general formula $$R-CH=C\begin{matrix}X\\COR^1\end{matrix} \qquad (II)$$

in which

R, R$^1$ and X have the above-mentioned meanings is reacted with an amine of the general formula $$R^2-NH_2 \qquad (IV)$$

and a β-ketocarboxylic acid ester of the general formula $$R^3-CO-CH_2-COO-A-Y \qquad (V)$$

in which

R$^2$, R$^3$, A and Y have the above-mentioned meanings, optionally in the presence of an inert organic solvent, or (C) a ylidene-β-dicarbonyl compound of the general formula $$R-CH=C\begin{matrix}CO-R^3\\COO-A-Y\end{matrix} \qquad (VI)$$

in which

R, R$^3$, A and Y have the above-mentioned meanings, is reacted with an enamino compound of the general formula $$\begin{matrix}R^1-C=CH-X\\|\\R^2-NH\end{matrix} \qquad (VII)$$

in which

R$^1$, R$^2$ and X have the above-mentioned meanings, optionally in the presence of an inert organic solvent, or (D) a ylidene-β-dicarbonyl compound of the formula (VI), as defined above, is reacted with an amine of the formula (IV) as defined above and a keto derivative of the general formula $$R^1-CO-CH_2-X \qquad (VIII)$$

in which

R$^2$, R$^1$ and X have the above-mentioned meanings, optionally in the presence of an inert organic solvent, or (E) an aldehyde of the general formula $$R-C\begin{matrix}H\\O\end{matrix} \qquad (IX)$$

in which

R has the above-mentioned meanings, is reacted with an enamino compound of the formula (VII) as defined above, and a β-ketocarboxylic acid ester of the formula (V) as defined above, optionally in the presence of an inert organic solvent, or (F) an aldehyde of the formula (IX) as defined above, is reacted with an enaminocarboxylic acid ester of the formula (III) as defined above and a keto derivative of the formula (VIII) as defined above, optionally in the presence of an inert organic solvent; the reaction variant A, B, C, D, E and F being carried out at a temperature between 20° and 150° C.

The 1,4-dihydropyridine derivatives according to the invention possess valuable pharmacological properties. By reason of their circulation-influencing action, they can be used as anti-hypertensive agents, so peripheral and cerebral vasodilators and as coronary therapeutic agents and are thus to be regarded as an advance in pharmacy.

The synthesis of the compounds according to the invention is illustrated by the following reaction equations, for which (2-cyanoethyl)-methyl 1,4-dihydro-2,6-dimethyl-4-(3'-nitrophenyl)-pyridine-3,5-dicarboxylate, (2-carbethoxyethyl)isopropyl 1,4-dihydro-2,6-dimethyl-4-(2'-nitrophenyl)-pyridine-3,5-dicarboxylate and (2-acetoxyethyl)-methyl 1,4-dihydro-2,6-dimethyl-4-(3'-methoxyphenyl)-pyridine-3,5-dicarboxylate are chosen as examples of starting materials.

(A)

[Reaction scheme showing 3-nitrophenyl intermediate with H$_3$COOC and COO—(CH$_2$)$_2$—CN groups reacting with loss of H$_2$O to form 1,4-dihydropyridine product]

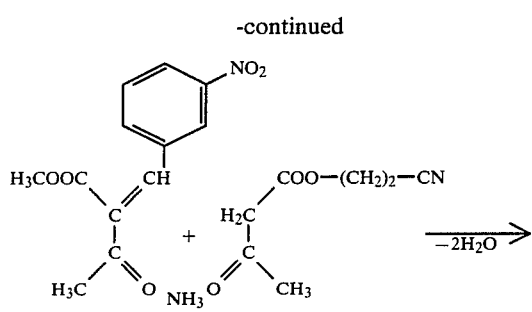
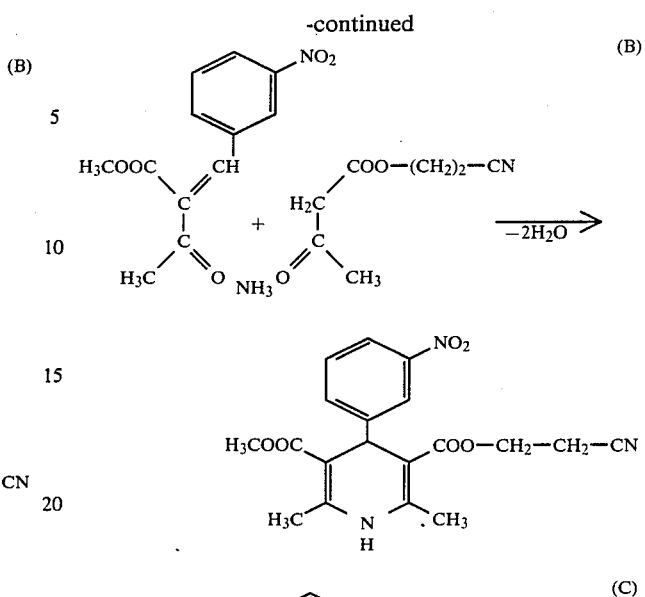
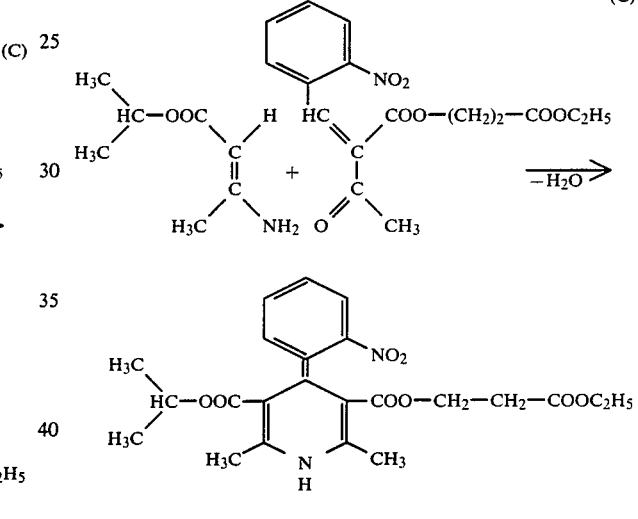
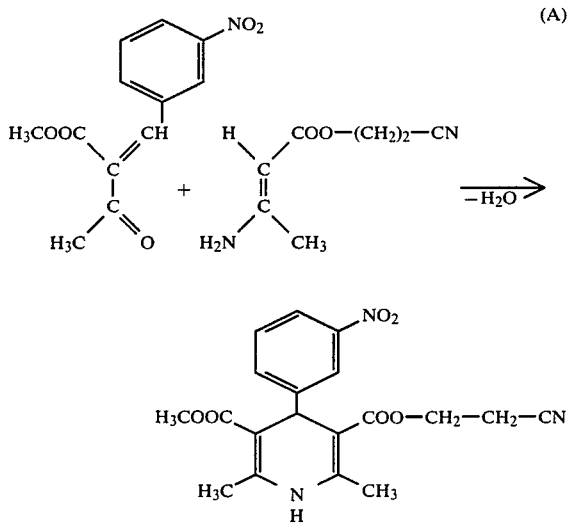

The following conditions apply to each of process variants A, B, C, D, E and F.

Dilients which can be used are all inert organic solvents. The solvent is preferably an alcohol, particularly an alkanol such as ethanol, methanol and isopropanol, an ether, such as dioxane, diethyl ether, tetrahydrofurane, glycol monomethyl ether and glycol dimethyl ether, or glacial acetic acid, dimethylformamide, dimethylsulphoxide, acetonitrile, pyridine or hexamethylphosphoric acid triamide.

The reaction temperatures can be varied within the relatively wide range of 20° to 150° C., but preferably at the boiling point of the particular solvent used. In the case of process variant A, the reaction is preferably carried out at between 20° and 100° C., and in particular at the boiling point of the particular solvent used.

The reaction can be carried out under normal pressure, but also under elevated pressure. In general, the reaction is carried out under normal pressure.

Dealing now with the process variant individually.

(1) PROCESS VARIANT A

According to process A, an ylidene compound of the formula

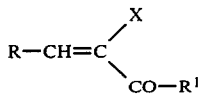
                                           (II)

is reacted with an enaminocarboxylic acid ester of the formula

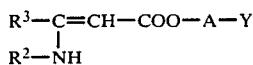
                                           (III)

In formula (II) R preferably denotes a phenyl or naphthyl radical or any of those heterocyclic radicals specified above for R. The said heterocyclic radicals and also, preferably, the phenyl radical optionally contain 1 or 2 identical or different substituents, substituents which may be mentioned being preferably phenyl, straight-chain or branched alkyl with 1 to 8 and especially 1 to 4 carbon atoms, cycloalkyl with 3 to 7 carbon atoms, alkenyl or alkinyl with 2 to 6 carbon atoms and especially 3 to 5 carbon atoms, tri-, tetra- and pentamethylene, dioxymethylene, halogen, such as fluorine, chlorine, bromine or iodine, especially fluorine, chlorine or bromine, trifluoromethyl, trifluoromethoxy, nitro, cyano, azido, hydroxyl, amino, mono- and dialkylamino with preferably 1 to 4 and especially 1 or 2 carbon atoms per alkyl group, carboxyl, carbalkoxy with preferably 2 to 4 and especially 2 or 3 carbon atoms, carboxamido, sulphonamido or $SO_m$-alkyl, in which m is 0, 1 or 2 and alkyl contains preferably 1 to 4 and especially 1 or 2 carbon atoms.

Furthermore, in formula (II) $R^1$ preferably denotes a hydrogen atom, a straight-chain or branched alkyl radical with 1 to 4 and especially 1 to 2 carbon atoms, a phenyl radical or an aralkyl radical, especially a benzyl radical; and when X denotes the group —CO—$R^6$, $R^6$ preferably denotes a straight-chain or branched alkyl radical with 1 to 4 carbon atoms, a phenyl radical, a benzyl radical, an amino or monoalkylamino group or a dialkylamino group with up to 4 carbon atoms per alkyl group, the alkyl groups optionally forming, together with the nitrogen atom, a 5-membered to 7-membered ring which optionally contains, as a further heteroatom, an oxygen or sulphur atom; or when X denotes the group —COOR$^7$, $R^7$ preferably denotes a straight-chain, branched or cyclic, saturated or unsaturated hydrocarbon radical with up to 8 and especially with up to 6 carbon atoms, which is optionally interrupted in the chain by an oxygen atom or a sulphur atom or by the —SO— or —SO$_2$ group and/or in which one hydrogen atom can be replaced by one or two trifluoromethyl groups or by a phenyl, phenoxy, phenylthio or phenylsulphonyl group, which is optionally substituted by halogen, especially fluorine, chlorine or bromine, cyano, dialkylamino with, in each case, 1 or 2 carbon atoms per alkyl group, alkoxy with 1 to 4 carbon atoms, alkyl with 1 to 4 carbon atoms, trifluoromethyl or nitro, or by an α-, β- or γ-pyridyl group or by an amino group, this amino group carrying two identical or different substituents selected from alkyl with up to 4 carbon atoms, alkoxyalkyl with up to 4 carbon atoms, phenyl and aralkyl, especially benzyl, and these substituents optionally forming, together with the nitrogen atom, a 5-membered to 7-membered ring which can contain, as a further hetero-atom, an oxygen or sulphur atom or the N-alkyl grouping, in which the alkyl group preferably comprises 1 to 3 carbon atoms; or when X denotes the group —COO—A'—Y', it being possible for this group to be identical or different to the radical —COO—A—Y as defined below and the definitions of A and A' and of Y and Y' correspoding to each other; or when X denotes the group —S(O)$_r$—$R^8$, r is 0, 1 or 2 and $R^8$ preferably denotes a straight-chain, branched or cyclic, saturated or unsaturated aliphatic hydrocarbon radical with up to 8 and especially up to 6 carbon atoms, which is optionally interrupted in the chain by 1 oxygen atom and/or in which one hydrogen atom is optionally replaced by a phenyl, phenoxy, phenylthio or phenylsulphonyl group, which is optionally substituted by halogen, especially fluorine, chlorine or bromine, cyano, dialkylamino with, in each case, 1 or 2 carbon atoms per alkyl group, alkoxy with 1 to 4 carbon atoms, alkyl with 1 to 4 carbon atoms, trifluoromethyl or nitro, or by an α-, β- or γ-pyridyl group or by an amino group, this amino group carrying two identical or different substituents from the group comprising alkyl with up to 4 carbon atoms, alkoxyalkyl with up to 6 and especially with up to 4 carbon atoms, phenyl and aralkyl, especially benzyl, and these substituents optionally forming, together with the nitrogen atom, a 5-membered to 7-membered ring, which can contain, as a further hetero-atom, an oxygen or sulphur atom or the N-alkyl grouping, in which the alkyl group preferably comprises 1 to 3 carbon atoms, or $R^8$ preferably denotes an aryl radical, especially a phenyl radical, which optionally carries 1, 2 or 3 identical or different substituents, substituents which may be mentioned being straight-chain or branched alkyl with 1 to 4 carbon atoms, alkoxy with 1 to 2 carbon atoms, halogen, especially fluorine, chlorine or bromine, cyano, trifluoromethyl, trifluoromethoxy, dialkylamino with, in each case, 1 to 2 carbon atoms per alkyl group or nitro.

The ylidene compounds of the formula (II) used as starting materials are known from the literature or can be prepared by methods known from the literature (compare, for example, G. Jones "The Knoevenagel Condensation" in Org. Reactions, vol. XV, 204 et seq. (1967) and G. Beck and D. Günther, Chem. Ber. 106, 2758 (1973)).

Examples which may be mentioned are: benzylideneacetylacetone, β,β-dibenzoylstyrene, 2'-nitrobenzylideneacetylacetone, methyl 2'-nitrobenzylideneacetoacetate, ethyl 3'-nitrobenzylideneacetoacetate, 2-cyanoethyl 3'-nitrobenzylideneacetoacetate, 2-carbethoxyethyl 3'-nitrobenzylideneacetoacetate, 2-acetoxyethyl 3'-nitrobenzylideneacetoacetate, 2-azidoethyl 3'-nitrobenzylideneacetoacetate, 2-nitroethyl 3'-nitrobenzylideneacetoacetate, n-butyl 2'-trifluoromethylbenzylideneacetoacetate, isopropyl 2'-cyanobenzylideneacetoacetate, cyclopentyl 3'-cyano-benzylideneacetoacetate, ethyl 2'-methylbenzylidene-acetoacetate, propargyl 2'-methoxybenzylideneacetoacetate, methyl 2'-propargyloxybenzylideneacetoacetate, methyl 2'-cyclopropylmethyloxybenzylideneacetoacetate, 2-methoxyethyl 2'-chlorobenzylideneacetoacetate, 2-methylthioethyl 2'-chlorobenzylideneacetoacetate, 2,2,2-trifluoroethyl 3'-nitrobenzylideneacetoacetate, 2,2,2-trifluoroethyl 2'-chlorobenzylideneacetoacetate, 2-dimethylaminoethyl 3'-chlorobenzylideneacetoacetate, 2-(piperidino-1)-ethyl 2'-bromobenzylideneacetoacetate, 2-(N-benzyl-N-methylamino)-ethyl 2'-fluorobenzylideneacetoacetate, propyl 3'-trifluoromethoxybenzylideneacetoacetate, methyl 2'-ethinylbenzylideneacetoacetate, ethyl 3'-azidobenzylideneacetoacetate, n-butyl 4′-methoxycarbonylbenzylideneacetoacetate, isopropyl 3′-methylsulphonylbenzylideneacetoacetate, cyclohexyl 3′-methylsulphonylbenzylideneacetoacetate, isobutyl 2′-nitrobenzylideneacetoacetate, benzyl 3′-chloro-4′-nitrobenzylideneacetoacetate, 4-chlorobenzyl 4′-chloro-3′-sulphamoylbenzylideneacetoacetate, 4-trifluoromethylbenzyl 3′,4′-dichlorobenzylideneacetoacetate, 2-phenoxyethyl 3′-cyanobenzylideneacetoacetate, 2-(2-pyridyl)-ethyl 2′-nitrobenzylideneacetoacetate, 2-(2-pyridyl)-ethyl 3′-nitrobenzylideneacetoacetate, 3′-nitrobenzylidene-acetoacetic acid amide, 2′-trifluoromethylbenzylideneacetoacetic acid dimethylamide, methyl 2′-nitrobenzylidenepropionylacetate, ethyl 2′-cyanobenzylidenepropionylacetate, methyl 2′-trifluoromethylbenzylidenebenzoylacetate, methyl 3′-azidobenzylidene-γ-phenylacetoacetate, methyl α-acetyl-β-(3-pyridyl)-acrylate, 2-n-propoxyethyl α-acetyl-β-(4-quinolinyl)-acrylate, ethyl α-acetyl-β-(2-thienyl)-acrylate, isobutyl α-acetyl-β-(2-furyl)-acrylate, 1-phenyl-2-methylsulphonyl-but-1-en-3-one, 1-(2′-nitrophenyl)-2-methylsulphonyl-but-1-en-3-one, 1-(3′-nitrophenyl)-2-ethylsulphonyl-but-1-en-3-one, 1-(2′-trifluoromethylphenyl)-2-methylsulphonyl-but-1-en-3-one, 1-(2′-cyanophenyl)-2-methylsulphonyl-but-1-en-3-one, 1-(2′-methylphenyl)-2-methylsulphonyl-but-1-en-3-one, 1-(2′-methoxyphenyl)-2-methylsulphonyl-but-1-en-3-one, 1-(2′-chlorophenyl)-2-methylsulphonyl-but-1-en-3-one, 1-(3′-cyanophenyl)-2-n-butylsulphonyl-but-1-en-3-one, 1-(2′-nitrophenyl)-2-(2-methoxyethylsulphonyl)-but-1-en-3-one, 1-(3′-nitrophenyl)-2-cyclopentylsulphonyl-but-1-en-3-one, 1-(2′-trifluoromethylphenyl)-2-(2-dimethylaminoethylsulphonyl)-but-1-en-3-one, 1-(2′-cyanophenyl-2-(2-(1-piperidino)-ethylsulphonyl)-but-1-en-3-one, 1-(2′-nitrophenyl)-2-(2-(N-benzyl-N-methylamino)-ethylsulphonyl)-but-1-en-3-one, 1-(3′-nitrophenyl)-2-benzylsulphonyl-but-1-en-3-one, 1-(3′-cyanophenyl)-2-(2-phenoxyethylsulphonyl)-but-1-en-3-one, 1-(3′-nitrophenyl)-2-(2-(2-pyridyl)-ethylsulphonyl)-but-1-en-3-one, 1-(2′-trifluoromethylphenyl)-2-phenylsulphonyl-but-1-en-3-one, 1-(2′-nitrophenyl)-2-(3-chlorophenylsulphonyl)-but-1-en-3-one, 1-(3′-nitrophenyl)-2-(4-methylphenylsulphonyl)-but-1-en-3-one, 1-(3′-nitrophenyl-2-(4-methoxyphenylsulphonyl)-but-1-en-3-one, 1-(2′-trifluoromethylphenyl)-2-(4-nitrophenylsulphonyl)-but-1-en-3-one, 1-(2′-nitrophenyl)-2-(4-trifluoromethylphenylsulphonyl)-but-1-en-3-one, 1-(2′-nitrophenyl)-2-methylsulphonyl-pent-1-en-3-one, 1-(3′-nitrophenyl)-2-methylsulphonyl-4-phenyl-but-1-en-3-one, 1-(2′-nitrophenyl)-2-phenylsulphonyl-3-phenylprop-1-en-3-one, 1-(3-pyridyl)-2-methylsulphonyl-but-1-en-3-one, 1-(2-pyridyl)-2-n-butylsulphonyl-but-1-en-3-one, 1-(3-pyridyl)-2-phenylsulphonyl-but-1-en-3-one, 1-(4-quinolinyl)-2-methylsulphonyl-but-1-en-3-one, 1-(2-thienyl)-2-(4-trifluoromethylphenylsulphonyl)-but-1-en-3-one and 1-(2-furyl)-2-(3,4-dichlorophenylsulphonyl)-but-1-en-3-one.

In formula (III) $R^2$ preferably denotes a hydrogen atom or denotes a straight-chain or branched alkyl radical with 1 to 8 carbon atoms and especially 1 to 4 carbon atoms, the alkyl radical optionally being interrupted in the alkyl chain by an oxygen atom, or denotes a phenyl radical or denotes an aralkyl radical, especially a benzyl radical, $R^3$ preferably denotes a hydrogen atom, a straight-chain or branched alkyl radical with 1 to 4 and especially with 1 or 2 carbon atoms, a phenyl radical or an aralkyl radical, especially a benzyl radical, A denotes a straight-chain, branched or cyclic aliphatic hydrocarbon radical with up to 12 carbon atoms and especially up to 6 carbon atoms, which is optionally substituted by an α-, β- or γ-pyridyl group or preferably by a phenyl group, which, in turn, can be substituted by halogen, especially by fluorine, chlorine or bromine, or by cyano, nitro, alkyl, alkoxy or dialkylamino with, in each case, 1 to 4 and especially 1 or 2 carbon atoms per alkyl group, or by trifluoromethyl and can contain up to a maximum of three identical or different substituents, and Y preferably denotes an azido, nitro or nitrile group or preferably denotes an ester group of the formula —COOR$^4$, in which R$^4$ denotes a straight-chain, branched or cyclic alkyl radical with up to 8 carbon atoms and especially with up to 6 carbon atoms, or denotes an aralkyl radical, especially the benzyl radical, or Y preferably denotes the group

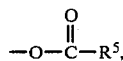

in which R$^5$ denotes a straight-chain, branched or cyclic, saturated or unsaturated alkyl radical with up to 12 carbon atoms and especially with up to 6 carbon atoms or preferably denotes a phenyl radical, which can contain 1 to 3 identical or different substituents selected from halogen, especially fluorine, chlorine or bromine, alkyl, alkoxy and dialkylamino with, in each case, 1 to 4 and preferably 1 or 2 carbon atoms per alkyl group, cyano, nitro and trifluoromethyl.

The enaminocarboxylic acid esters of the formula (III) which are used as starting materials can be prepared by methods known from the literature (compare A. C. Cope, J. Amer. Chem. Soc. 67, 1017 (1945)).

Examples which may be mentioned are: 2-cyanoethyl β-amino-crotonate, 2-nitroethyl β-amino-crotonate, 2-azidoethyl β-amino-crotonate, 2-cyanoethyl β-methylamino-crotonate, 2-cyanoethyl β-n-butylamino-crotonate, 2-cyanoethyl β-isobutylamino-crotonate, 2-cyanoethyl β-(2-methoxyethylamino)-crotonate, 2-cyanoethyl β-anilino-crotonate, 2-cyanoethyl β-benzylamino-crotonate, 2-cyanoethyl β-amino-β-propyl-acrylate, 2-cyanoethyl β-amino-cinnamate, 2-cyanoethyl β-amino-β-benzyl-acrylate, 1-cyanoethyl β-amino-crotonate, 3-cyanopropyl β-amino-crotonate, 3-cyano-n-butyl β-amino-crotonate, 3-cyano-3-phenylpropyl β-amino-crotonate, 2-cyano-1-methyl-ethyl β-amino-crotonate, α-cyano-benzyl β-amino-crotonate, 3-cyano-cyclopentyl β-amino-o-crotonate, 4-cyano-cyclohexyl β-amino-crotonate, 3-cyano-3-(α-pyridyl)-propyl β-amino-crotonate, 3-cyano-3-(3-chlorophenyl)-propyl β-amino-crotonate, 3-cyano-3-(3′-nitrophenyl)-propyl β-amino-crotonate, 3-cyano-3-p-toluene-propyl β-amino-crotonate, 3-cyano-3-(4-methoxyphenyl)-propyl β-amino-crotonate, 3-cyano-3-(4-dimethylaminophenyl)-propyl β-amino-crotonate, 3-cyano-3-(4-trifluoromethylphenyl)-propyl β-amino-crotonate, 3-cyano-3-(3,4-dichlorophenyl)-propyl β-amino-crotonate, 3-cyano-3-(2,4-dichlorophenyl)-propyl β-amino-crotonate, 3-cyano-(3,4,5-trimethoxyphenyl)-propyl β-amino-crotonate, 3-cyano-3-(3-chloro-4-methylphenyl)-propyl β-amino-crotonate, 3-cyano-3-(3-chloro-4-trifluoromethylphenyl)-propyl β-amino-crotonate, 2-ethoxycarbonyl-ethyl β-amino-crotonate, 2-n-butoxycarbonylethyl β-amino-crotonate, 2-isopropoxycarbonylethyl β-amino-crotonate, 2-cyclopentyloxycarbonyl-ethyl β-amino-crotonate, 2-benzoyloxycarbonyl-ethyl β-amino-crotonate, α-methoxycarbonylbenzyl β-amino-crotonate, 1-methoxycarbonyl-ethyl β-amino-crotonate, 4-amyloxycarbonyl-cyclohexyl ε-amino-crotonate, 2-acetoxy-ethyl β-amino-crotonate, 2-isobutyroyloxy-ethyl β-amino-crotonate, 2-benzoyloxy-ethyl ε-amino-crotonate, 2-(4-chlorobenzoyloxy)-ethyl β-amino-crotonate, 2-(4-tert.-butylbenzoyloxy)-ethyl β-amino-crotonate, 2-(4-methoxybenzoyloxy)-ethyl β-amino-crotonate, 2-(4-dimethylaminobenzoyloxy)-ethyl β-amino-crotonate, 2-(3,4-dichlorobenzoyloxy)-ethyl β-amino-crotonate, 2-(3-chloro-4-methyl-benzoyloxy)-pthyl β-amino-crotonate, 2-(4-trifluoromethylbenzoyloxy)-ethyl β-amino-crotonate, 2-(3-cyanobenzoyloxy)-ethyl β-amino-crotonate, 2-(4-nitrobenzoyloxy)-ethyl β-amino-crotonate and 2-(3-nitrobenzoyloxy)-ethyl β-amino-crotonate.

When carrying out the process according to the invention, one mol of the ylidene compound of the formula (II) is reacted with one mol of the enaminocarboxylic acid ester of the formula (III) in a suitable solvent. The isolation and purification of the substances according to the invention is preferably effected by distilling off the solvent in vacuo and recrystallising the residue, which in some cases is obtained in the crystalline form only after ice-cooling, from a suitable solvent.

(2) PROCESS VARIANT B

According to process B, an ylidene compound of the formula

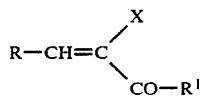

is reacted with an amine of the formula (IV) and a β-ketocarboxylic acid ester of the formula (V)

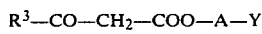

In the formulae (II), (IV) and (V), the radicals R, $R^1$, $R^2$, $R^3$, X, A and Y have the preferred meanings indicated under process variant A.

Examples of the ylidene compounds of the formula (II) which are used as starting substances have already been listed under process variant A.

The amines of the formula (IV) which can be used according to the invention are already known.

Examples which may be mentioned are: ammonia, methylamine, n-propylamine, isopropylamine, n-butylamine, isobutylamine, β-methoxyethylamine, benzylamine and aniline.

The β-ketocarboxylic acid esters of the formula (V) which are used as starting materials can be prepared by methods known from the literature (for example D. Borrmann, "Umsetzung von Diketen mit Alkoholen, Phenolen und Mercaptanen" ("Reaction of Diketene with Alcohols, Phenols and Mercaptans") in Houben-Weyl, Methoden der Organischen Chemie (Methods of Organic Chemistry), volume VII/4, 230 et seq. (1968)).

Examples which may be mentioned are: 2-cyanoethyl acetoacetate, 2-cyanoethyl propionylacetate, 2-cyanoethyl γ-phenylacetoacetate, 2-cyanoethyl benzoylacetate, 2-azidoethyl acetoacetate, 2-nitroethyl acetoacetate, 3-cyanopropyl acetoacetate, 3-cyano-n-butyl acetoacetate, 2-cyano-1-methyl-ethyl acetoacetate, α-cyano-benzyl acetoacetate, 3-cyano-cyclopentyl acetoacetate, 4-cyano-cyclohexyl acetoacetate, 3-cyano-3-phenyl-propyl acetoacetate, 3-cyano-3-(α-pyridyl)-propyl acetoacetate, 3-cyano-3-(3'-chlorophenyl)-propyl acetoacetate, 3-cyano-3-(3'-nitrophenyl)-propyl acetoacetate, 3-cyano-3-p-tolyl-propyl acetoacetate, 3-cyano-3-(4-methoxyphenyl)-propyl acetoacetate, 3-cyano-3-(4-dimethylaminophenyl)-propyl acetoacetate, 3-cyano-3-(4-trifluoromethylphenyl)-propyl acetoacetate, 3-cyano-3-(3,4-dichlorophenyl)-propyl acetoacetate, 3-cyano-3-(2,4-dichlorophenyl)-propyl acetoacetate, 3-cyano-3-(3,4,5-trimethoxyphenyl)-propyl acetoacetate, 3-cyano-3-(3-chloro-4-methylphenyl)-propyl acetoacetate, 3-cyano-3-(3-chloro-4-trifluoromethylphenyl)-propyl acetoacetate, 2-ethoxycarbonyl-ethyl acetoacetate, 2-n-butyoxycarbonyl-ethyl acetoacetate, 2-isopropoxycarbonyl-ethyl acetoacetate, 2-cyclopentyloxycarbonyl-ethyl acetoacetate, 2-benzyloxycarbonyl-ethyl acetoacetate, α-methoxycarbonyl-benzyl acetoacetate, 1-methoxycarbonyl-ethyl acetoacetate, 4-allyloxycarbonylcyclohexyl acetoacetate, 2-acetoxy-ethyl acetoacetate, 2-isobutyroyloxy-ethyl acetoacetate, 2-benzoyloxy-ethyl acetoacetate, 2-(4-chlorobenzoyl)-ethyl acetoacetate, 2-(4-tert.-butylbenzoyloxy)-ethyl acetoacetate, 2-(4-methoxybenzoyloxy)-ethyl acetoacetate, 2-(4-dimethylaminobenzoyloxy)-ethyl acetoacetate, 2-(3,4-dichlorobenzoyloxy)-ethyl acetoacetate, 2-(3-chloro-4-methyl-benzoyloxy)-ethyl acetoacetate, 2-(4-trifluoromethylbenzoyloxy)-ethyl acetoacetate, 2-(3-cyanobenzoyloxy)-ethyl acetoacetate, 2-(4-nitrobenzoyloxy)-ethyl acetoacetate and 2-(3-nitrobenzoyloxy)-ethyl acetoacetate.

When carrying out the process according to the invention, the substances of the formulae (II), (IV) and (V) which participate in the reaction are each employed in molar amounts. The compounds according to the invention can be purified easily by recrystallisation from a suitable solvent.

(3) PROCESS VARIANT C

According to process C, an ylidene-β-dicarbonyl compound of the formula

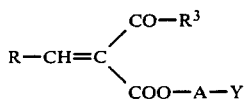

is reacted with an enamino compound of the formula

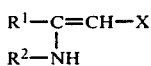

In the formulae (VI) and (VII), R, $R^1$, $R^2$, $R^3$, A, X and Y preferably have the meaning indicated under process variant A.

The ylidene-β-dicarbonyl compounds of the formula (VI) which are used as starting materials can be prepared by methods known from the literature (compare, for example, G. Jones, "The Knoevenagel Condensation" in Org. Reactions, Vol. XV, 204 et seq. (1967)).

Examples which may be mentioned are: 2-cyanoethyl 2'-nitrobenzylidene-acetoacetate, 3-cyanopropyl 3'-nitrobenzylidene-acetoacetate, 2-azidoethyl 2'-chlorobenzylideneacetoacetate, 2-nitroethyl 2'-trifluoromethylbenzilidene-acetoacetate, 3-cyano-n-butyl 2'-methoxybenzylidene-acetoacetate, 2-cyano-1-methyl-ethyl 3'-methylbenzylidene-acetoacetate, α-cyanobenzyl 2'-chlorobenzylidene-acetoacetate, 3-cyanocyclopentyl 3'-bromobenzylidene-acetoacetate, 4-cyano-cyclohexyl 3'-cyanobenzylidene-acetoacetate, 3-cyano-3-phenyl-propyl 2'-trifluoromethylbenzylidene-acetoacetate, 3-cyano-3-(α-pyridyl)-propyl 3'-trifluoromethylbenzylidene-acetoacetate, 3-cyano-3-(3-chlorophenyl)-propyl 3'-trifluoromethoxybenzylidene-acetoacetate, 3-cyano-3-(3'-nitrophenyl)-propyl 3',4'-dioxymethylenebenzylidene-acetoacetate, 3-cyano-3-p-tolyl-propyl 2'-propargylbenzylidene-acetoacetate, 3-cyano-3-(4-methoxy-phenyl)-propyl 2'-allylbenzylidene-acetoacetate, 3-cyano-3-(4-trifluoromethylphenyl)-propyl 2'-propargyloxybenzylidene-acetoacetate, 3-cyano-3-(4-dimethylaminophenyl)-propyl 3'-methylsulphonylbenzylidene-acetoacetate, 3-cyano-3-(3,4-dichlorophenyl)-propyl 3',4'-tetramethylenebenzylidene-acetoacetate, 3-cyano-3-(2,4-dichlorophenyl)-propyl 2-acetyl-3-(3-pyridyl)-acrylate, 3-cyano-3-(3,4,5-trimethoxyphenyl)-propyl 2-acetyl-3-(2-thienyl)-acrylate, 3-cyano-3-(3-chloro-4-methylphenyl)-propyl 2-acetyl-3-(2-furyl)-acrylate, 3-cyano-3-(3-chloro-4-trifluoromethylphenyl)-propyl 2-acetyl-3-(4-quinolyl)-acrylate, 3-cyano-3-(4-bromo-3-trifluoromethylphenyl)-propyl 2-acetyl-3-(2-pyridyl)-acrylate, 2-ethoxycarbonyl-ethyl 3'-nitrobenzylidene-acetoacetate, 2-n-butoxycarbonyl-ethyl 3'-nitro-4'-chlorobenzylidene-acetoacetate, 2-isopropoxycarbonyl-ethyl 2'-nitrobenzylidene-acetoacetate, 2-benzyloxycarbonyl-ethyl 2'-trifluoromethylbenzylidene-acetoacetate, α-methoxycarbonyl-benzyl 2'-chlorobenzylidene-acetoacetate, 1-methoxycarbonyl-ethyl 3'-cyanobenzylidene-acetoacetate, 2-acetoxy-ethyl 3'-methoxybenzylidene-acetoacetate, 2-benzoyloxy-ethyl 3'-methoxy-4'-chlorobenzylidene-acetoacetate, 2-(4-chlorobenzoyloxy)-ethyl 3'-nitrobenzylidene-acetoacetate, 2-(4-tert.-butylbenzoyloxy)-ethyl 4'-nitrobenzylidene-acetoacetate, 2(4-methoxybenzoyloxy)-ethyl 2'-nitrobenzylidene-acetoacetate, 2-(4-dimethylaminobenzoyloxy)-ethyl 3'-trifluoromethylbenzylidene-acetoacetate, 2-(3,4-dichlorobenzoyloxy)-ethyl 3'-nitrobenzylidene-acetoacetate, 2-(3-chloro-4-methylbenzoyloxy)-ethyl 3'-nitrobenzylidene-acetoacetate, 2-(4-trifluoromethylbenzoyloxy)-ethyl 2'-trifluoromethylbenzylidene-acetoacetate, 2-(3-cyanobenzoyloxy)-ethyl 2'-fluorobenzylidene-acetoacetate, 2-(4-nitrobenzoyloxy)-ethyl 2'-chlorobenzylidene-acetoacetate and 2-(3-nitrobenzoyloxy)-ethyl 2,4-dichlorobenzylidene-acetoacetate.

The enamino compounds of the formula (VII) which are used as starting materials are known from the literature or can be prepared by methods known from the literature (compare A. C. Cope, J. Amer. Chem. Soc. 67, 1017 (1945) and N. Guruswamy et al. Indian J. Chem. 11, 882 (1973)).

Examples which may be mentioned are: 4-amino-3-penten-2-one, 3-amino-1,3-diphenyl-acrolein, 4-amino-5-diphenyl-3-penten-2-one, β-aminocrotonamide, β-aminocrotonic acid n-butylamide, β-aminocrotonic acid dimethylamide, methyl β-aminocrotonate, n-butyl β-aminocrotonate, isopropyl β-amino-crotonate, cyclopentyl β-aminocrotonate, allyl β-amino-crotonate, 2,2,2-trifluoroethyl β-aminocrotonate, 2,2,2-trifluoro-1-trifluoromethyl-ethyl β-aminocrotonate, n-butyl β-methylaminocrotonate, isopropyl β-n-butylamino-crotonate, cyclopentyl β-benzylaminocrotonate, allyl β-(2-methoxyethylamino)-crotonate, propargyl β-aniline-crotonate, 2-methoxy-ethyl β-amino-β-ethylacrylate, 2-propoxyethyl β-amino-β-benzyl-acrylate, benzyl β-aminocrotonate, 2-phenylethyl β-aminocrotonate, 2-phenoxyethyl β-aminocrotonate, 2-phenylthioethyl β-aminocrotonate, 2-phenylsulphonylethyl β-aminocrotonate, 2-methylthioethyl β-aminocrotonate, 2-ethylthio-ethyl β-aminocrotonate, 2-methylsulphonylethyl β-aminocrotonate, 4-chlorobenzyl β-aminocrotonate, methoxybenzyl β-aminocrotonate, 4-methylbenzyl β-aminocrotonate, 4-trifluoromethylbenzyl β-aminocrotonate, 3,4-dichlorobenzyl β-aminocrotonate, pyridyl-2-methyl β-aminocrotonate, 2-dimethylaminoethyl β-aminocrotonate, 2-(N-benzyl-N-methylamino)-ethyl β-aminocrotonate, 2-(1-piperidino)-ethyl β-aminocrotonate, 2-(4-morpholino)-ethyl β-aminocrotonate, 2-amino-1-methylsulphonyl-prop-1-ene, 2-amino-1-methylsulphonyl-but-1-ene, 2-amino-β-methylsulphonylstyrene, 2-amino-1-ethylsulphonyl-but-1-ene, 2-amino-1-isobutylsulphonyl-prop-1-ene, 2-amino-1-cyclopentylsulphonyl-prop-1-ene, 2-amino-1-(2-methoxyethylsulphonyl)-prop-1-ene, 2-amino-1-(2-propoxyethylsulphonyl)-prop-1-ene, 2-amino-1-(benzylsulphonyl)-prop-1-ene, 2-amino-1-(2-phenoxyethylsulphonyl)-prop-1-ene, 2-amino-1-(2-dimethylaminoethylsulphonyl)-prop-1-ene, 2-amino-1-(2-N-benzyl-N-methylaminoethylsulphonyl)-prop-1-ene, 2-methylamino-1-methylsulphonyl-prop-1-ene, 2-methylamino-1-ethylsulphonyl-prop-1-ene, 2-ethylamino-1-benzylsulphonyl-prop-1-ene, 2-amino-1-phenylsulphonyl-prop-1-ene, 2-amino-1-(4-chlorophenylsulphonyl)-prop-1-ene, 2-amino-1-(4-methylphenylsulphonyl)-prop-1-ene, 2-amino-1-(4-methoxyphenylsulphonyl)-prop-1-ene, 2-amino-1-(4-trifluoromethylphenylsulphonyl)-prop-1-ene, 2-amino-1-(4-nitrophenylsulphonyl)-prop-1-ene, 2-amino-1-(4-trifluoromethoxyphenylsulphonyl)-prop-1-ene, 2-amino-1-(3,4-dichlorophenylsulphonyl)-prop-1-ene and 2-amino-1-(4-chloro-3-trifluoromethylphenylsulphonyl)-prop-1-ene.

When carrying out the process according to the invention, one mol of the ylidene-β-dicarbonyl compound of the formula VI is reacted with one mol of the enamino compound of the formula VII in a suitable solvent.

(4) PROCESS VARIANT D

According to process D, an ylidene-β-dicarbonyl compound of the formula

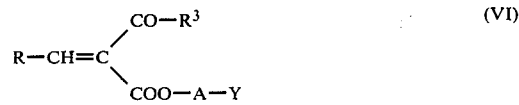

is reacted with an amine of the formula (IV) and a keto derivative of the formula (VIII)

In the formulae (VI), (IV) and (VIII), the radicals R, $R^1$, $R^2$, $R^3$, A, X and Y preferably have the meaning indicated under process variant A.

Examples of the ylidene-β-dicarbonyl compounds of the formula (VI) which are used as starting compounds have already been listed under process variant C.

The amines of the formula (IV) which can be used according to the invention have already been described under process variant B.

The keto derivatives of the formula (VIII) which are employed as starting substances are known from the literature or can be prepared by methods known from the literature (compare, for example, D. Borrmann, "Umsetzung von Diketen mit Alkoholen, Phenolen und Mercaptanen" ("Reaction of Diketene with Alcohols, Phenols and Mercaptans"), in Houben-Weyl, Methoden der Organischen Chemie (Methods of Organic Chemistry), vol. VII/4, 230 et seq. (1968); H. O. House and J. K. Larson, J. Org. Chem. 33, 61 (1968)).

Examples which may be mentioned are: acetylacetone, benzoylacetone, ω-benzylacetophenone, acetoacetamide, acetoacetic acid n-butylamide, acetoacetic acid dimethylamide, ethyl formylacetate, methyl acetoacetate, ethyl n-propionylacetate, ethyl benzoylacetate, isopropyl acetoacetate, cyclopentyl acetoacetate, allyl acetoacetate, propargyl acetoacetate, 2-methoxy-ethyl acetoacetate, 2,2,2-trifluoroethyl acetoacetate, 2,2,2-trifluoro-1-trifluoromethyl-ethyl acetoacetate, 2-propoxyethyl acetoacetate, benzyl acetoacetate, 2-phenylethyl acetoacetate, 2-phenoxyethyl acetoacetate, 2-phenylthioethyl acetoacetate, 2-phenylsulphonylethyl acetoacetate, 2-methylthioethyl acetoacetate, 2-methylsulphonylethyl acetoacetate, 2-benzylthioethyl acetoacetate, pyridyl-2-methyl acetoacetate, 2-dimethylaminoethyl acetoacetate, 2-(N-benzyl-N-methylamino)-ethyl acetoacetate, 2-(1-piperidino)-ethyl acetoacetate, 2-(4-morpholino)-ethyl acetoacetate, methylsulphonylacetone, n-butylsulphonylacetone, isobutylsulphonylacetone, cyclopentylsulphonylacetone, (2-methoxyethylsulphonyl)-acetone, (2-propoxyethylsulphonyl)-acetone, benzylsulphonylacetone, 4-chlorobenzylsulphonylacetone, 4-trifluoromethylbenzylsulphonylacetone, (2-phenylethylsulphonyl)-acetone, (2-phenoxyethylsulphonyl)-acetone, (2-dimethylaminoethylsulphonyl)-acetone, (2-N-benzyl-N-methylamino-ethylsulphonyl)-acetone, (2(1-piperidino)-ethylsulphonyl)-acetone, phenylsulphonylacetone, 4-chlorophenylsulphonylacetone, 4-fluorophenylsulphonylacetone, 3,4-dichlorophenylsulphonylacetone, 4-trifluoromethylphenylsulphonylacetone, 4-trifluoromethoxyphenylsulphonylacetone, 4-chloro-3-trifluoromethylphenylsulphonylacetone, 4-methylphenylsulphonylacetone, 4-tert.-butylphenylsulphonylacetone, 4-methoxyphenylsulphonylacetone, 4-nitrophenylsulphonylacetone and 4-methylsulphonylacetone.

When carrying out the process according to the invention, the substances of the formula (VI), (IV) and (VIII) which participate in the reaction are in each case added in molar amounts.

The compounds according to the invention can be purified easily by recrystallisation from a suitable solvent.

(5) PROCESS VARIANT E

According to process E, an aldehyde of the formula

   (IX)

is reacted with an enamino compound of the formula

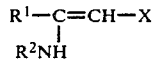   (VII)

and a β-keto-carboxylic acid ester of the formula $R^3$—CO—CH$_2$—COO—A—Y   (V)

In the formulae (IX) and (V), R, $R^1$, $R^2$, $R^3$, A. X and Y preferably have the meaning indicated under process variant A.

The aldehydes of the formula (IX) which are used as starting materials are known from the literature or can be prepared by methods known from the literature (compare, for example, E. Mosettig, Org. Reactions VIII, 218 et seq. (1954)).

Examples which may be mentioned are: benzaldehyde, 2-, 3- or 4-phenylbenzaldehyde, α- or β-naphthylaldehyde, 2-, 3- or 4-methylbenzaldehyde, 2- or 4-n-butylbenzaldehyde, 2-, 3- or 4-isopropylbenzaldehyde, 2- or 4-cyclopropylbenzaldehyde, 2-vinylbenzaldehyde, 2-ethinylbenzaldehyde, 2,3-tetramethylenebenzaldehyde, 3,4-dioxymethylenebenzaldehyde, 2-, 3- or 4-methoxybenzaldehyde, 2-cyclopropylmethyloxybenzaldehyde, 2-propargyloxybenzaldehyde, 2-allyloxybenzaldehyde, 2-, 3- or 4-chloro bromo/-fluoro-benzaldehyde, 2-, 3- or 4-trifluoromethylbenzaldehyde, 2-, 3- or 4-trifluoromethoxybenzaldehyde, 4-hydroxybenzaldehyde, 2-, 3- or 4-nitrobenzaldehyde, 2-, 3- or 4-cyanobenzaldehyde, 3-azidobenzaldehyde, 2-, 3- or 4-dimethylaminobenzaldehyde, 3-carboethoxybenzaldehyde, 3- or 4-carbamoylbenzaldehyde, 2-, 3- or 4-methylmercaptobenzaldehyde, 2-, 3- or 4-methylsulphinylbenzaldehyde, 2-, 3- or 4-methylsulphonylbenzaldehyde, 3,4,5-trimethoxybenzaldehyde, 2,4- or 2,6-dichlorobenzaldehyde, 2,4-dimethylbenzaldehyde, 2,4- or 2,6-dinitrobenzaldehyde, 2-chloro-6-nitrobenzaldehyde, 4-chloro-2-nitrobenzaldehyde, 2-nitro-4-methoxybenzaldehyde, 2-nitro-4-cyanobenzaldehyde, 2-chloro-4-cyanobenzaldehyde, 4-cyano-2-methylbenzaldehyde, 3-methyl-4-trifluoromethylbenzaldehyde, 3-chloro-4-trifluoromethylbenzaldehyde and 4-chloro-3-sulphamoylbenzaldehyde, thiophene-2-aldehyde, furane-2-aldehyde, pyrrole-2-aldehyde, pyrazole-4-aldehyde, imidazole-2-aldehyde, oxazole-2-aldehyde, isoxazole-3-aldehyde, thiazole-2-aldehyde, pyridine-2-aldehyde, pyridine-3-aldehyde, pyridine-4-aldehyde, 4-methyl-pyridine-2-aldehyde, 6-methylpyridine-2-aldehyde, pyridazine-4-aldehyde, pyrimidine-4-aldehyde, pyrazine-2-aldehyde, quinoline-4-aldehyde, isoquinoline-1-aldehyde, indole-3-aldehyde, benzimidazole-2-aldehyde, quinazoline-2-aldehyde and quinoxaline-2-aldehyde.

The enamino compounds of the formula (VII) which can be used according to the invention have already been indicated under process variant C and the β-ketocarboxylic acid esters of the formula (V) which are employed according to the invention have already been indicated under process variant B.

When carrying out the process according to the invention, the substances of the formulae (IX), (VII) and (V) which participate in the reaction are in each case employed in molar amounts.

(6) PROCESS VARIANT F

According to process F, an aldehyde of the formula

   (IX)

is reacted with an enaminocarboxylic acid ester of the formula

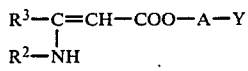 (III)

and a keto derivative of the formula

 (VIII)

In the formulae (IX), (III) and (VIII), R, $R^1$, $R^2$, $R^3$, A, X and Y preferably have the meaning indicated under process variant A.

The aldehydes of the formula (IX) used as starting substances have been listed under process variant E, the enaminocarboxylic acid esters of the formula (III) have been listed under process variant A and the keto derivatives of the formula (VIII) have been listed under process variant D.

When carrying out the process according to the invention, the substances of the formula (IX), (III) and (VIII) which participate in the reaction are in each case preferably employed in approximately molar amount.

In order to avoid a prolix presentation, reactants have been exemplified for each process variant; and it is to be understood that the disclosure includes each specific final product obtainable by each process variant. Thus, the specific reaction products are all contemplated where one reacts Reactants II and III according to Process Variant A; where one reacts Reactants II, IV and V according to Process Variant B; where one reacts Reactants VI and VII according to Process Varient C; where one reacts Reactants VI, IV and VIII according to Process Variant D; where one reacts Reactant IX, VII and V according to Process Varient E and where one reacts Reactants IX, III and VIII according to Process Variant F.

Depending on the starting substances chosen, the compounds according to the invention can exist in stereoisomeric forms, which either behave as image and mirror image (enantiomers) or do not behave as image and mirror image (diastereomers). The present invention relates not only to the antipodes but also to the racemic forms and to the mixtures of diastereomers. The racemic forms, like the diastereomers, can be separated in a known manner into the constituents which constitute single stereoisomers (compare, for example, E. L. Eliel, Stereochemistry of Carbon Compounds, McGraw Hill, 1962). A resulting basic compound can be converted into a corresponding acid addition salt, for example by reacting it with an inorganic or organic acid, such as therapeutically useful acid, or with a corresponding anion exchange preparation, and isolating the desired salt. An acid addition salt may be converted into the free compound by treatment with a base, e.g. a metal hydroxide, ammonia or a hydroxyl ion exchange preparation. Therapeutically useful acids are, for example, inorganic acids, e.g. hydrochloric, hydrobromic, sulfuric, phosphoric, nitric or perchloric acid, or organic acids, e.g. carboxylic or sulfonic acids, such as formic, acetic, propionic, succinic, glycollic, lactic, malic, tartaric, citric, ascorbic, maleic, hydroxymaleic, pyroracemic, phenylacetic, benzoic, 4-aminobenzoic, anthranilic, 4-hydroxybenzoic, salicyclic, aminosalicyclic, embonic, nicotinic, methanesulfonic, ethanesulfonic, hydroxy-ethanesulfonic, ethylenesulfonic, benzenesulfonic, halogenobenzenesulfonic, toluensulfonic, naphthalenesulfonic and sulfanilic acid; methionine, tryptophan, lysine and arginine.

Salts of the above-mentioned acids or other salts, for example, the picrates, can also be used for purification of the bases obtained; the bases are converted into salts, the salts are separated and the bases are liberated from the salts. In view of the close relationship between the free compounds and the compounds in the form of their salts, whenever a compound is referred to in this context, a corresponding salt is also intended, provided such is possible or appropriate under the circumstances.

Compounds according to the invention which are particularly preferred are those of the general formula I in which R denotes a phenyl radical which is optionally substituted by 1 or 2 substituents selected from trifluoromethyl, nitro, halogen, cyano, azido, alkoxy with 1 to 4 carbon atoms and alkyl with 1 to 4 carbon atoms, or denotes a pyridyl radical, $R^1$ and $R^3$ are identical or different and denote an alkyl group with 1 to 4 carbon atoms and especially 1 or 2 carbon atoms, $R^2$ denotes a hydrogen atom, an alkyl group with 1 to 4 carbon atoms or a benzyl radical, A denotes a straight-chain or branched alkylene group with up to 4 carbon atoms, which is optionally substituted by phenyl or pyridyl, Y denotes an azido, nitro or nitrile group or denotes an ester group of the formula $—COOR^4$, in which $R^4$ denotes an alkyl group with 1 to 4 carbon atoms, or denotes the group $O—CO—R^5$, in which $R^5$ denotes an alkyl group with 1 to 4 carbon atoms, and X denotes the group $—COOR^7$, in which $R^7$ denotes a straight-chain, branched or cyclic, saturated or unsaturated hydrocarbon radical with up to 6 carbon atoms, which is optionally interrupted in the chain by an oxygen or sulphur atom and which is optionally substituted by trifluoromethyl, amino or alkylamino or dialkylamino, each with 1 to 4 carbon atoms in the alkyl groups, or denotes the group $—COO—A'—Y'$, this group being identical or different to the moiety $—COO—A—Y$ of formula (I) and $A'$ and $Y'$ having any of those meanings given for A and Y respectively or denotes the group $—SO_2—R^8$, in which $R^8$ denotes straight-chain or branched alkyl group with up to 6 carbon atoms, which is optionally interrupted in the chain by an oxygen atom.

In addition to those specified in the Examples, the following are preferred active compounds according to the invention: methyl 2-cyanoethyl 1,4-dihydro-2,6-dimethyl-4-(2'-trifluoromethylphenyl)-pyridine-3,5-dicarboxylate, isopropyl 2-cyanoethyl 1,4-dihydro-2,6-dimethyl-4-(2'-trifluoromethylphenyl)-pyridine-3,5-dicarboxylate, ethyl 2-cyanoethyl 1,4-dihydro-2,6-dimethyl-4-(2'-nitrophenyl)-pyridine-3,5-dicarboxylate, isobutyl 2-cyanoethyl 1,4-dihydro-2,6-dimethyl-4-(2'-nitrophenyl)-pyridine-3,5-dicarboxylate, cyclopentyl 2-cyanoethyl 1,4-dihydro-2,6-dimethyl-4-(2'-nitrophenyl)-pyridine-3,5-dicarboxylate, propargyl 2-cyanoethyl 1,4-dihydro-2,6-dimethyl-4-(3'-nitrophenyl)-pyridine-3,5-dicarboxylate, 2-propoxyethyl 2-cyanoethyl 1,4-dihydro-2,6-dimethyl-4-(3'-nitrophenyl)-pyridine-3,5-dicarboxylate, 4-chlorobenzyl 2-cyanoethyl 1,4-dihydro-2,6-dimethyl-4-(3'-nitrophenyl)-pyridine-3,5-dicarboxylate, 3,4-dichlorobenzyl 2-cyanoethyl 1,4-dihydro-2,6-dimethyl-4-(3'-nitrophenyl)-pyridine-3,5-dicarboxylate, 3,4,5-trimethoxybenzyl 2-cyanoethyl 1,4-dihydro-2,6-dimethyl-4-(3'-nitrophenyl)-pyridine-3,5-dicarboxylate, 2-(benzyl-methylamino)-ethyl 2-cyanoethyl 1,4-dihydro-2,6-dimethyl-4-(3'-nitrophenyl)-pyridine-3,5-dicarboxylate, methyl α-methoxycarbonyl-4-chlorobenzyl 1,4-dihydro-2,6-dimethyl-4-(3'-nitrophenyl)-pyridine-3,5-dicarboxylate, methyl α-methoxycarbonyl-4-trifluoromethylbenzyl 1,4-dihydro-2,6-dimethyl-4-(3'-nitrophenyl)-pyridine-3,5-dicarboxylate, ethyl α-ethoxycarbonyl-3,4-dichlorobenzyl 1,4-dihydro-2,6-dimethyl-4-(3'-nitrophenyl)-pyridine-3,5-dicarboxylate, isopropyl 2-carbethoxyethyl 1,4-dihydro-2,6-dimethyl-4-(3'-nitrophenyl)-pyridine-3,5-dicarboxylate, 2,2,2-trifluoroethyl 2-cyanoethyl 1,4-dihydro-2,6-dimethyl-4-(3'-nitrophenyl)-pyridine-3,5-dicarboxylate, 2,2,2-trifluoroethyl α-methoxycarbonylbenzyl 1,4-dihydro-2,6-dimethyl-4-(3'-nitrophenyl)-pyridine-3,5-dicarboxylate, 2,2,2-trifluoroethyl 2-carbethoxyethyl 1,4-dihydro-2,6-dimethyl-4-(3'-nitrophenyl)-pyridine-3,5-dicarboxylate, 2,2,2-trifluoroethyl 2-acetoxyethyl 1,4-dihydro-2,6-dimethyl-4-(3'-nitrophenyl)-pyridine-3,5-dicarboxylate, 2,2,2-trifluoroethyl 2-benzoyloxyethyl 1,4-dihydro-2,6-dimethyl-4-(3'-nitrophenyl)-pyridine-3,5-dicarboxylate and 2,2,2-trifluoroethyl 2-(4-chlorobenzoyloxy)-ethyl 1,4-dihydro-2,6-dimethyl-4-(3'-nitrophenyl)-pyridine-3,5-dicarboxylate.

The new compounds have a broad and diverse pharmacological action spectrum.

In detail, the following main actions are demonstrable in animal experiments:

1. On parenteral, oral and perlingual administration the compounds produce a distinct and long-lasting dilation of the coronary vessels. This action on the coronary vessels is intensified by a simultaneous nitrite-like effect of reducing the load on the heart. They influence or modify the heart metabolism in the sense of an energy saving.
2. The excitability of the stimulus formation and excitation conduction system within the heart is lowered, so that an anti-fibrillation action demonstrable at therapeutic doses results.
3. The tone of the smooth muscle of the vessels is greatly reduced under the action of the compounds. This vascular-spasmolytic action can take place in the entire vascular system or can manifest itself more or less isolated in circumscribed vascular regions (such as, for example, the central nervous system).
4. The compounds lower the blood pressure of hypertonic animals and can thus be used as antihypertensive agents.
5. The compounds have strongly muscular-spasmolytic actions which manifest themselves on the smooth muscle of the stomach, the intestinal tract, the urogenital tract and the respiratory system.

As stated above, the invention also relates to the use in medicine of the compounds of the invention.

The present invention provides a pharmaceutical composition containing as active ingredient a compound of the invention in admixture with a solid liquid or liquefied gaseous diluent.

The invention further provides a pharmaceutical composition containing as active ingredient a compound of the invention in the form of a sterile and/or physiologically isotonic aqueous solution.

The invention also provides a medicament in dosage unit form comprising a compound of the invention.

The invention also provides a medicament in the form of tablets (including lozenges and granules), dragees, capsules, pills, ampoules or suppositories comprising a compound of the invention.

"Medicament" as used in this Specification means physically discrete coherent portions suitable for medical administration. "Medicament in dosage unit form" as used in this Specification means physically discrete coherent units suitable for medical administration each containing a daily dose or a multiple (up to four times) or sub-multiple (down to a fortieth) of a daily dose of the compound of the invention in association with a carrier and/or enclosed within an envelope. Whether the medicament contains a daily dose or, for example, a half, a third or a quarter of a daily dose will depend on whether the medicament is to be administered once or, for example, twice, three times or four times a day respectively.

The pharmaceutical compositions according to the invention may, for example, take the form of suspensions, solutions and emulsions of the active ingredient in aqueous or non-aqueous diluents, syrups, granulates or powders.

The diluents to be used in pharmaceutical compositions (e.g. granulates) adapted to be formed into tablets, dragees, capsules and pills include the following: (a) fillers and extenders, e.g. starch, sugers, mannitol, and silicic acid; (b) binding agents, e.g. carboxymethyl cellulose and other cellulose derivatives, alginates, gelatine and polyvinyl pyrrolidone; (c) moisturizing agents, e.g. glycerol; (d) disintegrating agents, e.g. agaragar, calcium carbonate and sodium bicarbonate; (e) agents for retarding dissolution e.g. paraffin (f) resorption accelerators, e.g, quaternary ammonium compounds; (g) surface active agents, e.g. cetyl alcohol, glycerol monostearate; (h) adsorptive carriers, e.g. kaolin and bentonite; (i) lubricants, e.g. talc, calcium and magnesium stearate and solid polyethyl glycols.

The tablets, dragees, capsules and pills formed from the pharmaceutical compositions of the invention can have the customary coatings, envelopes and protective matrices, which may contain opacifiers. They can be so constituted that they release the active ingredient only or preferably in a particular part of the intestinal tract, possibly over a period of time. The coatings, envelopes and protective matrices may be made, for example, of polymeric substances or waxes.

The ingredient can also be made up in microencapsulated form together with one or several of the above-mentioned diluents.

The diluents to be used in pharmaceutical compositions adapted to be formed into suppositories can, for example, be the usual water-soluble diluents, such as polyethylene glycols and fats (e.g. cocoa oil and high esters [e.g. $C_{14}$-alcohol with $C_{16}$-fatty acid]) or mixtures of these diluents.

The pharmaceutical compositions which are solutions and emulsions can, for example, contain the customary diluents (with, of course, the above-mentioned exclusion of solvents having a molecular weight below 200 except in the presence of a surface-active agent), such as solvents, dissolving agents and emulsifiers; specific examples of such diluents are water, ethyl alcohol, isopropyl alcohol, ethyl carbonate, ethyl acetate, benzyl alcohol, benzyl benzoate, propylene glycol, 1,3-butylene glycol, dimethylformamide, oils [for example ground nut oil], glycerol, tetrahydrofurfuryl alcohol, polyethylene glycols and fatty acid esters of sorbitol or mixtures thereof.

For parenteral administration, solutions and emulsions should be sterile, and, if appropriate, blood-isotonic.

The pharmaceutical compositions which are suspensions can contain the usual diluents, such as liquid diluents, e.g. water, ethyl alcoho, propylene glycol, surface-active agents (e.g. ethoxylated isostearyl alcohols, polyoxyethylene sorbite sand sorbitane esters), microcrystalline cellulose, aluminium metahydroxide, bentonite, agar-agar and tragacanth or mixtures thereof.

All the pharmaceutical compositions according to the invention can also contain colouring agents and preservatives as well as perfumes and flavouring additions (e.g. peppermint oil and eucalyptus oil) and sweetening agents (e.g. saccharin).

The pharmaceutical compositions according to the invention generally contain from 0.5 to 90% of the active ingredient by weight of the total composition.

In addition to a compound of the invention, the pharmaceutical compositions and medicaments according to the invention can also contain other pharmaceutically active compounds. They may also contain a plurality of compounds of the invention.

Any diluent in the medicaments of the present invention may be any of those mentioned above in relation to the pharmaceutical compositions of the present invention. Such medicaments may include solvents of molecular weight less than 200 as sole diluent.

The discrete coherent portions constituting the medicament according to the invention will generally be adapted by virtue of their shape or packaging for medical administration and may be, for example, any of the following: tablets (including lozenges and granulates), pills, dragees, capsules, suppositories and ampoules. Some of these forms may be made up for delayed release of the active ingredient. Some, such as capsules, include a protective envelope which renders the portions of the medicament physically discrete and coherent.

The preferred daily dose for administration of the medicaments of the invention is 2.5 to 250 mg of active ingredient in the case of intravenous administration and 25 to 250 mg of active ingredient in the case of oral administration.

The product of the above-mentioned pharmaceutical compositions and medicaments is carried out by any method known in the art, for example, by mixing the active ingredient(s) with the diluent(s) to form a pharmaceutical composition (e.g. a granulate) and then forming the composition into the medicament (e.g. tablets).

This invention further provides a method for combating the above-mentioned diseases in warm-blooded animals, which comprises administering to the animals a compound of the invention alone or in admixture with a diluent or in the form of a medicament according to the invention.

It is envisaged that these active compounds will be administered perorally, parenterally (for example intramuscularly, intraperitoneally, subcutaneously and intravenously), rectally or locally, preferably orally or parenterally, especially perlingually or intravenously. Preferred pharmaceutical compositions and medicaments are therefore those adapted for administration such as oral or parenteral administration. Administration in the method of the invention is preferably oral or parenteral administration.

In general it has proved advantageous to administer intravenously amounts of from 0.01 mg to 10 mg/kg, preferably 0.05 to 5 mg/kg, of body weight per day and to administer orally 0.05 to 20 mg/kg, preferably 0.5 mg to 5 mg/kg, of body weight per day, to achieve effective results. Nevertheless, it can at times be necessary to deviate from those dosage rates, and in particular to do so as a function of the nature and body weight of the human or animal subject to be treated, the individual reaction of this subject to the treatment, and type of formulation in which the active ingredient is administered and the mode in which the administration is carried out, and the point in the progress of the disease or interval at which it is to be administered. Thus it may in some case suffice to use less than the above-mentioned minimum dosage rate. whilst other cases the upper limit mentioned must be exceeded to achieve the desired results. Where larger amounts are administered it can be advisable to divide these into several individual administrations over the course of the day.

The following Examples illustrate the preparation of compounds of the present invention.

EXAMPLE 1

Ethyl 2-cyanoethyl 1,4-dihydro-2,6-dimethyl-4-(2-trifluoromethylphenyl)-pyridine-3,5dicarboxylate

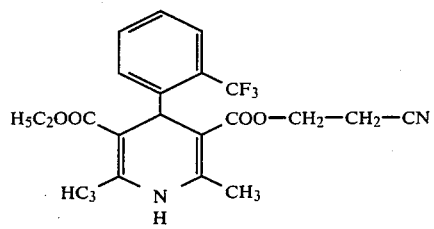

PROCESS VARAINT A

A solution of 18.6 g (75 mmols) of ethyl 2'-trifluoromethylbenzylideneacetoacetate and 11.6 g (75 mmols) of 2-cyanoethyl 3-aminocrotonate in 120 ml of ethanol is heated at the boil for 12 hours. After cooling the reaction mixture, the solvent is distilled off in vacuo and the oily residue is treated with a little ether and made to crystallise. The product is filtered off and recyrstallised from ethanol.
Melting point: 126° C.
Yield: 21 g (66%)

PROCESS VARIANT E

A solution of 13 g (75 mmols) of 2-trifluoromethylbenzaldehyde, 9.7 g (75 mmols) of ethyl β-amino-crotonate and 11.6 g (75 mmols) of 2-cyanoethyl aceto-acetate in 120 ml of ethanol is heated under reflux for 15 hours. The solvent is then distilled off in vacuo and the oily residue is treated with a little ether and made to crystallise. The product is filtered off and recyrstallised from ethanol.
Melting point: 126° C.
Yield: 17.5 g (55%)

The following compounds in Table 1 are obtained analogously to Example 1 using corresponding starting materials:

TABLE 1

| Example No. | Formula | Solvent | Melting point | Yield |
|---|---|---|---|---|
| 2 | 2-nitrophenyl dihydropyridine: methyl ester and 2-cyanoethyl ester, with 2,6-dimethyl-1,4-dihydropyridine core | Methanol | 154° C. | 48% |
| 3 | 3-nitrophenyl analog with methyl ester and 2-cyanoethyl ester | Methanol | 135° C. | 55% |
| 4 | 3-nitrophenyl analog with ethyl ester ($H_5C_2O_2C$) and 2-cyanoethyl ester | Ethanol | 152° C. | 63% |
| 5 | 3-nitrophenyl analog with isopropyl ester and 2-cyanoethyl ester | Ethanol | 141° C. | 68% |
| 6 | 3-nitrophenyl analog with sec-butyl ester and 2-cyanoethyl ester | Dimethyl-formamide | 106° C. | 60% |
| 7 | 3-nitrophenyl analog with cyclopentyl ester and 2-cyanoethyl ester | Ethanol | 131° C. | 66% |

TABLE 1-continued
| Example No. | Formula | Solvent | Melting point | Yield |
|---|---|---|---|---|
| 8 | 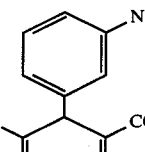 | Ethanol | 142° C. | 45% |
| 9 | 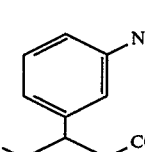 | Ethanol | 141° C. | 58% |
| 10 | 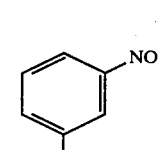 | Ethanol | 152° C. | 71% |
| 11 | 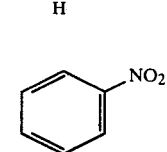 | Ethanol | Oil | 45% |
| 12 | 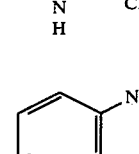 | HMPT | 117° C. | 68% |
| 13 | 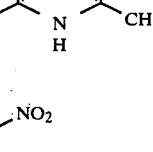 | Isopropanol | 183° C. | 45% |

TABLE 1-continued

| Example No. | Formula | Solvent | Melting point | Yield |
|---|---|---|---|---|
| 14 | 4-(3-nitrophenyl)-3-(isopropoxycarbonyl)-5-(1-cyanoethyl oxycarbonyl)-2,6-dimethyl-1,4-dihydropyridine | Ethanol | 123° C. | 40% |
| 15 | 4-(3-nitrophenyl)-3,5-bis(2-cyanoethoxycarbonyl)-2,6-dimethyl-1,4-dihydropyridine | Ethanol | 166° C. | 65% |
| 16 | 4-(3-nitrophenyl)-3-(phenylsulfonyl)-5-(2-cyanoethoxycarbonyl)-2,6-dimethyl-1,4-dihydropyridine | HMPT | 161° C. | 62% |
| 17 | 4-(3-chlorophenyl)-3-(ethoxycarbonyl)-5-(2-cyanoethoxycarbonyl)-2,6-dimethyl-1,4-dihydropyridine | Ethanol | Oil | 51% |
| 18 | 4-(4-methoxy-2,6-disubstituted phenyl)-3-(ethoxycarbonyl)-5-(2-cyanoethoxycarbonyl)-2,6-dimethyl-1,4-dihydropyridine | Ethanol | 132° C. | 51% |
| 19 | 4-(3-pyridyl)-3-(ethoxycarbonyl)-5-(2-cyanoethoxycarbonyl)-2,6-dimethyl-1,4-dihydropyridine | Ethanol | 195° C. | 56% |

TABLE 1-continued
| Example No. | Formula | Solvent | Melting point | Yield |
|---|---|---|---|---|
| 20 | 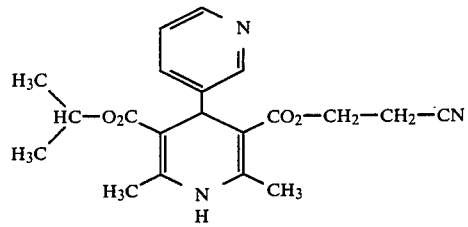 | Iso-propanol | 192° C. | 49% |
| 21 | 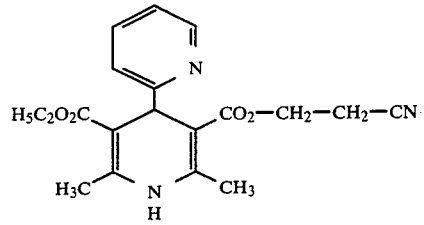 | Ethanol | 169° C. | 70% |
| 22 | 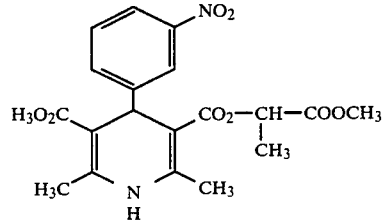 | Methanol | 189° C. | 63% |
| 23 | 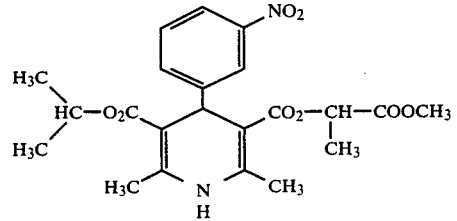 | Methanol | 137° C. | 51% |
| 24 | 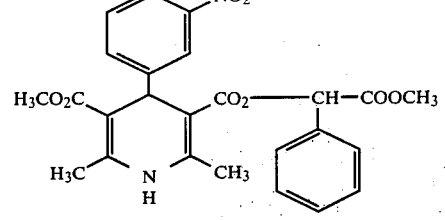 | Methanol | 177° C. | 55% |
| 25 | 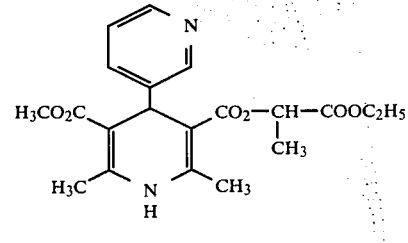 | Ethanol | 100° C. | 75% |

TABLE 1-continued

| Example No. | Formula | Solvent | Melting point | Yield |
|---|---|---|---|---|
| 26 | 3,5-bis(2-acetoxyethoxycarbonyl)-2,6-dimethyl-4-phenyl-1,4-dihydropyridine | Ethanol | 86° C. | 50% |
| 27 | 3,5-bis(2-acetoxyethoxycarbonyl)-4-(2-chlorophenyl)-2,6-dimethyl-1,4-dihydropyridine | Ethanol | 104° C. | 60% |
| 28 | 3,5-bis(2-acetoxyethoxycarbonyl)-4-(3-chlorophenyl)-2,6-dimethyl-1,4-dihydropyridine | Ethanol | 88° C. | 45% |
| 29 | 3,5-bis(2-acetoxyethoxycarbonyl)-2,6-dimethyl-4-(4-nitrophenyl)-1,4-dihydropyridine | Ethanol | 146° C. | 68% |
| 30 | 3,5-bis(2-acetoxyethoxycarbonyl)-4-(2-methoxyphenyl)-2,6-dimethyl-1,4-dihydropyridine | Ethanol | 110° C. | 50% |
| 31 | 3,5-bis(2-acetoxyethoxycarbonyl)-2,6-dimethyl-4-(3-methylphenyl)-1,4-dihydropyridine | Ethanol | 94° C. | 60% |

TABLE 1-continued

| Example No. | Formula | Solvent | Melting point | Yield |
|---|---|---|---|---|
| 32 | 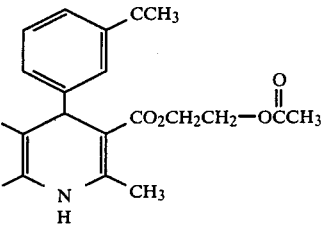 | Ethanol | 70° C. | 80% |
| 33 | 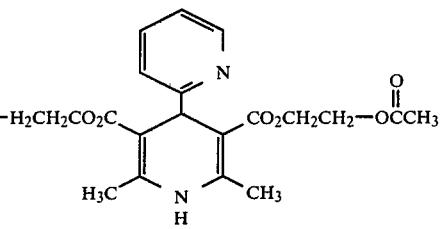 | Ethanol | 116° C. | 52% |
| 34 | 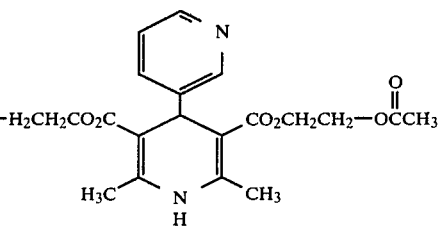 | Ethanol | 110° C. | 75% |
| 35 | 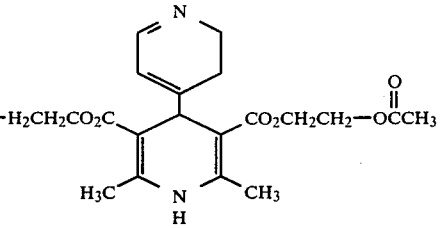 | Ethanol | 120° C. | 50% |
| 36 | 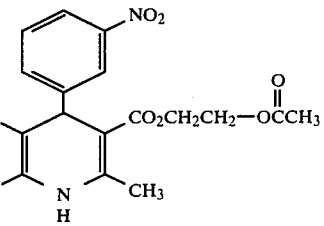 | Ethanol | 124° C. | 40% |
| 37 | 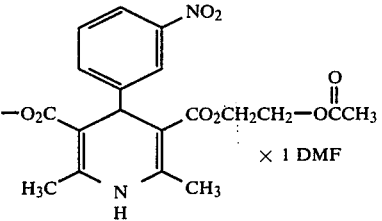 | DMF | 89° C. | 63% |

Among the new 1,4-dihydropyridine salts of the invention, those salts that are pharmaceutically acceptable are particularly important and are preferred.

The new free 1,4-dihydropyridines of the general formula I and their salts can be interconverted in any suitable manner; methods for such interconversion are known in the art.

The present invention also comprises pharmaceutically acceptable bioprecursors of the active compounds of the present invention.

For the purposes of this specification the term 'pharmaceutically acceptable bioprecursor' of an active compound of the invention means a compound having a structural formula different from the active compound but which nonetheless, upon administration to an animal or human being is converted in the patient's body to the active compound.

We claim:

1. A compound of the formula I

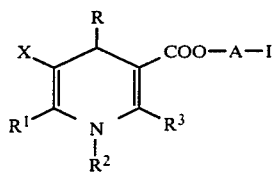

or a salt thereof in which

R denotes a phenyl radical which is optionally substituted by one or two substituents selected from trifluoromethyl, nitro, halogen and cyano, or denotes a pyridyl radical, $R^1$ and $R^3$ are identical or different and denote an alkyl group with 1 to 4 carbon atoms, $R^2$ denotes a hydrogen atom or an alkyl group with 1 to 4 carbon atoms, A denotes a straight-chain or branched alkylene group with up to 4 carbon atoms, Y denotes a nitrile group and X denotes the group —$COOR^7$, in which $R^7$ denotes a straight-chain, branched or cyclic, saturated or unsaturated hydrocarbon radical with up to 6 carbon atoms which is optionally interrupted in the chain by an oxygen atom and which is optionally substituted by trifluoromethyl.

2. Compounds according to claim 1, in which $R^1$ and $R^3$ are identical or different and each is an alkyl group with 1 or 2 carbon atoms.

3. A compound according to claim 1 which is ethyl-2-cyanoethyl-1,4-dihydro-2,6-dimethyl-4-(2-trifluoromethylphenyl)-pyridine-3,5-dicarboxylate.

4. A compound according to claim 1 which is methyl-2-cyanoethyl-1,4-dihydro-2,6-dimethyl-4-(3-nitrophenyl)-pyridine-3,5-dicarboxylate.

5. A compound according to claim 1 which is isopropyl-2-cyanoethyl-1,4-dihydro-2,5-dimethyl-4-(3-nitrophenyl)-pyridine-3,5-dicaboxylate.

6. A compound according to claim 1 which is β-methoxy-ethyl-2-cyanoethyl-1,4-dihydro-2,5-dimethyl-4-(3-nitrophenyl)-pyridine-3,5-dicarboxylate.

7. A pharmaceutical composition containing as an active ingredient an effective vasodilating influencing amount of a compound according to claim 1 in admixture with a solid, liquid or liquefied gaseous diluent.

8. A pharmaceutical composition of claim 7 in the form of a sterile or physiologically isotonic aqueous solution.

9. A composition according to claim 7 or 8 containing from 0.5 to 90% by weight of the said active ingredient.

10. A medicament in dosage unit form comprising an effective vasodilating amount of a compound according to claim 1 and an inert pharmaceutical carrier.

11. A medicament of claim 10 in the form of a tablet, pill, dragee, capsule, ampoule, or suppository.

12. A method of effecting vasodilation in warm-blooded animals which comprises administering to the animals an effective vasodilation amount of an active compound according to claim 1 either alone or in admixture with a diluent or in the form of a medicament.

13. A method according to claim 12 in which the active compound is administered intravenously in an amount of 0.01 to 10 mg per kg body weight per day.

14. A method according to claim 13 in which the active compound is administered intravenously in an amount of 0.05 to 5 mg per kg body weight per day.

15. A method according to claim 12 in which the active compound is administered orally in an amount of 0.05 to 20 mg per kg body weight per day.

16. A method according to claim 15 in which the active compound is administered orally in an amount of 0.5 to 5 mg per kg body weight per day.

UNITED STATES PATENT AND TRADEMARK OFFICE
CERTIFICATE OF CORRECTION

PATENT NO. : 4,551,467

DATED : November 5, 1985

INVENTOR(S) : Egbert Wehinger, et al.

It is certified that error appears in the above-identified patent and that said Letters Patent is hereby corrected as shown below:

| | |
|---|---|
| Col. 1, line 22 and Col. 35, line 15 | Upper right of formula delete "COO-A-I" and substitute --COO-A-Y-- |
| Col. 16, line 4 | Insert --, (VII)-- after "(IX)" |
| Col. 21, line 8 | Delete "sand" and insert --and-- |
| Col. 36, line 9 | Delete "dicaboxylate" and substitute --dicarboxylate-- |
| Col. 36, line 14 | Delete "influexing" after "vasodilating" |

Signed and Sealed this

Eleventh Day of March 1986

[SEAL]

Attest:

DONALD J. QUIGG

Attesting Officer

Commissioner of Patents and Trademarks